US009886750B2

(12) United States Patent
Price et al.

(10) Patent No.: US 9,886,750 B2
(45) Date of Patent: Feb. 6, 2018

(54) ELECTRONIC DEVICE FOR READING DIAGNOSTIC TEST RESULTS AND COLLECTING SUBJECT DATA FOR INCLUSION IN A LOCAL CHAIN OF EVIDENCE DATABASE AND FOR TRANSFERRING AND RECEIVING DATA FROM REMOTE DATABASES

(71) Applicant: LifeSaver Int'l Inc, Mission Viejo, CA (US)

(72) Inventors: William Pat Price, Henderson, NV (US); Ted Titmus, Mission Viejo, CA (US)

( * ) Notice: Subject to any disclaimer, the term of this patent is extended or adjusted under 35 U.S.C. 154(b) by 274 days.

(21) Appl. No.: 14/707,244

(22) Filed: May 8, 2015

(65) Prior Publication Data
US 2015/0350605 A1 Dec. 3, 2015

Related U.S. Application Data (60) Provisional application No. 61/990,160, filed on May 8, 2014, provisional application No. 62/027,323, filed on Jul. 22, 2014.

(51) Int. Cl.
*G06K 9/00* (2006.01)
*G06T 7/00* (2017.01)
*G01N 33/52* (2006.01)
*G01N 21/27* (2006.01)
*A61B 5/00* (2006.01)
*A61B 5/11* (2006.01)
*A61B 5/1172* (2016.01)
*A61B 5/145* (2006.01)

(52) U.S. Cl.
CPC .......... *G06T 7/0004* (2013.01); *A61B 5/0062* (2013.01); *A61B 5/0077* (2013.01); *A61B 5/1112* (2013.01); *A61B 5/1172* (2013.01); *A61B 5/14507* (2013.01); *A61B 5/4277* (2013.01); *G01N 21/27* (2013.01); *G01N 33/526* (2013.01); *G06K 9/00013* (2013.01); *A61B 2562/0295* (2013.01); *A61B 2562/08* (2013.01); *A61B 2576/00* (2013.01)

(58) Field of Classification Search
CPC .......... G06K 9/00–9/2054; A61B 1/00; A61B 10/00; A61B 5/0062; A61B 5/0077; A61B 5/1112; A61B 5/1172; A61B 5/14507; A61B 5/4277; A61B 2562/0295; A61B 2562/08; A61B 2576/00; G01N 33/526; G01N 21/27; G06T 7/00
USPC ....................................................... 382/124
See application file for complete search history.

(56) References Cited

U.S. PATENT DOCUMENTS 9,360,490 B2* 6/2016 Green ................. G01N 33/84
2014/0315221 A1* 10/2014 Morsey ............. A61B 10/0051
435/7.34

* cited by examiner

*Primary Examiner* — Gregory F Cunningham
(74) *Attorney, Agent, or Firm* — Law Office of Scott C Harris, Inc (57) ABSTRACT

An electronic device for reading diagnostic test results and collecting subject data for inclusion in a local chain of evidence database and for transferring and receiving data from remote databases.

8 Claims, 6 Drawing Sheets

ELECTRONIC DEVICE FOR READING DIAGNOSTIC TEST RESULTS AND COLLECTING SUBJECT DATA FOR INCLUSION IN A LOCAL CHAIN OF EVIDENCE DATABASE AND FOR TRANSFERRING AND RECEIVING DATA FROM REMOTE DATABASES

This application claims priority from provisional No. 61/990,160, filed May 8, 2014, and from provisional No. 62/027,323 filed Jul. 22, 2014, the entire contents of both of which are herewith incorporated by reference.

FIELD OF INVENTION

The field of invention relates to the electronic collection of saliva based diagnostic test results, collection and documentation of bio-data relating to test subjects, and wireless communications for archiving and retrieval of related data.

BACKGROUND

Diagnostic testing using saliva based tests has made strides in recent years. Most saliva based testing requires substantial amount of oral fluid, on the order of five milliliters or more. New protocols for saliva based testing use small thin pads with antigens or reagents printed into the pads. This form of testing allows for very small amounts of oral fluids to saturate the pads and interact with the printed antigens and reagents causing them to change colors.

These types of testing devices and protocols are idea for use in the field with first responders, EMT, law enforcement, field medical personnel, military, and other personnel who normally administrate diagnostic testing. For example, law enforcement officers who suspect that someone driving a motor vehicle is under the influence will typically administrate a field sobriety test and/or have the individual blow into a portable breathalyzer. Field breathalyzers are notorious for being inaccurate judging by the number of tests disallowed by the courts. The ideal test protocol would be for an arresting officer to transport a suspect to a hospital for drawing blood or for a urine test. The drawback to this is that the body metabolizes approximately an ounce of 80 proof alcohol an hour. The time delay in administering a blood test may be sufficient for the suspect's body to metabolize a sufficient amount of alcohol such that the blood/alcohol ration drops below the level it had been when the suspect was arrested.

A next drawback to blood testing or urine testing is the amount of time it takes to process the sample which can range from hours to days to weeks. Easy to administrate saliva testing using in the mouth testing protocols returns the results in time increments from seconds to a few minutes.

Blood tests for single substances such as alcohol generally cost in the range of 30 to 50 dollars per test. Multiple substance testing quickly raises the cost to hundreds of dollars. Using blood for large screening efforts such as malaria, AIDs, and other debilitating and contagious pathogens quickly becomes unaffordable.

In mouth saliva based testing is relatively inexpensive when compared to blood and urine testing. For example, in mouth saliva based testing for multiple issues simply requires that multiple test pads be placed on a single appliance such as a stick that is placed in a test subject's mouth. If the test stick contains a separate test pad for malaria, AIDs, TB, and cholera. These this bank of tests were to be conducted using blood protocols the results could take weeks and the cost could run to hundreds of dollars. For example, a border patrol agent of any country who apprehends a group of people illegally crossing the border, can administer all of the tests using a single stick with four test pads and have the results within two to three minutes. This allows the agents to segregate a group of people into subgroups of those who have contagious illness of persons who need immediate medical care and those who are healthy.

SUMMARY

The inventors recognize that what is needed is needed is some way to record the test results of in-field saliva testing such that the person(s) administrating the testing can collect the results for chain of evidence and for inclusion into on-line databases.

The present invention is a portable or mobile hand held device designed that collects real time data from optical results of saliva based tests. The invention records tests and can upload results to databases and can record results to storage devices include write-once device to preserve chain of custody. The invention gives first responds, EMTs, medical personnel, law enforcement personnel, military personnel, and others the ability to administrate diagnostic tests and interpret the results in seconds.

DETAILED DESCRIPTION OF THE INVENTION

Embodiments

Reference will now be made in detail to various embodiments, examples of which are illustrated in the accompanying drawings. Wherever possible, the same reference numbers will be used throughout the drawings to refer to the same or like parts.

In a preferred embodiment the invention will allow a test administrator to insert a saliva based test stick into a slot residing on the invention. The test stick supports at least one saliva based test pad and a two dimensional scan code identifying the test strip on the same side of the test stick. The invention will read the results of the at least one saliva based test pad by optically scanning the test result pattern on the at least one saliva saturated test pad residing on the test stick and will read the value of the two dimensional scan code. The test result will be presented as a single line (a "−" dash line indicating a negative result) or a cross ("+" indicating a positive result) or no marking (" " indicating that the pad was not sufficiently saturated with saliva for the test to be conducted). In this preferred embodiment, the at least one saliva based test pad and the unique two dimensional scan code will be scanned by an optical edge scanner residing internal to the invention and the scanned image analyzed by a software algorithm to determine the marking indication or the lack of a marking indication of the at least one test pad and the unique alpha numeric coded two dimensional scan code. The software algorithm will then write the results of the at least one saliva based test pad and the value of the unique scan code to an event file. The test administrator will then insert the test subjects ID card into a slot on the invention. A software algorithm will scan the ID card with an optical edge scanner and analyze the scanned image and obtain text of the ID card and then write the ID text and scanned image of the ID card to the event file. The test administrator will then have the test subject swipe their thumbprint or all ten fingers across a fingerprint scanner. The invention will scan and write the user's thumbprint or fingerprints to the event file. The invention will then capture additional metadata associated with the test subject such as GPS location, time of day, weather conditions, test administrator's ID, and other associated metadata and write the metadata to the event file. The event file will be retained in a local data store and/or transmitted to an on-line database.

In another preferred embodiment the invention will allow a test administrator to photograph both sides of a saliva based test stick and both sides of a test subject's ID card with a camera contained within the invention. The saliva based test stick will have at least one saliva based test pad and a two dimensional scan code identifying the test strip. The invention will read the results of the at least one saliva based test pad and the unique two dimensional scan code image on the photograph by a software algorithm. The test result on the at least one saliva based test pad will be presented as a single line (a "−" dash line indicating a negative result) or a cross ("+" indicating a positive result) or no marking (" " indicating that the pad was not sufficiently saturated with saliva for the test to be conducted). The results of the at least one saliva based test pad and the value for the unique two dimensional scan code will be written to an event file. The test administrator will then photograph the both sides of the test subjects ID card and a software algorithm will analyze the photograph and obtain text of the ID card then write the ID card text and the ID card photograph to the event file. The invention will then capture additional metadata associated with the test subject such as GPS location, time of day, weather conditions, test administrator's ID, and other associated metadata and write the metadata to the event file. The event file will be retained in a local data store and/or transmitted to an on-line database.

In another preferred embodiment the invention will allow a test administrator to photograph, with a camera contained within the invention, both sides of a saliva based test stick supporting at least one test pad and a two dimensional scan code identifying the test strip, photograph both sides of the test subject's ID card, and photograph the test subject's face, any physical identifying features such as scars, tattoos, physical amoralities, gang dress or any other distinguishing features. The test result of the at least one test pad will be presented as a single line (a "−" dash line indicating a negative result) or a cross ("+" indicating a positive result) or no marking (" " indicating that the pad was not sufficiently saturated with saliva for the test to be conducted). The test administrator will manually interpret the results shown on the at least one test pad and of the value of the unique two dimensional scan code, the results of which along with the data contained on the test subject's ID card will be manually entered into data entry fields displayed on the invention's display screen. The invention will then write the resulting photographs, test result(s), and the value of the unique scan code, along with additional metadata, into an "event file" and retained in a local data store and/or transmitted to an on-line database.

Software Stack

Figure 1:
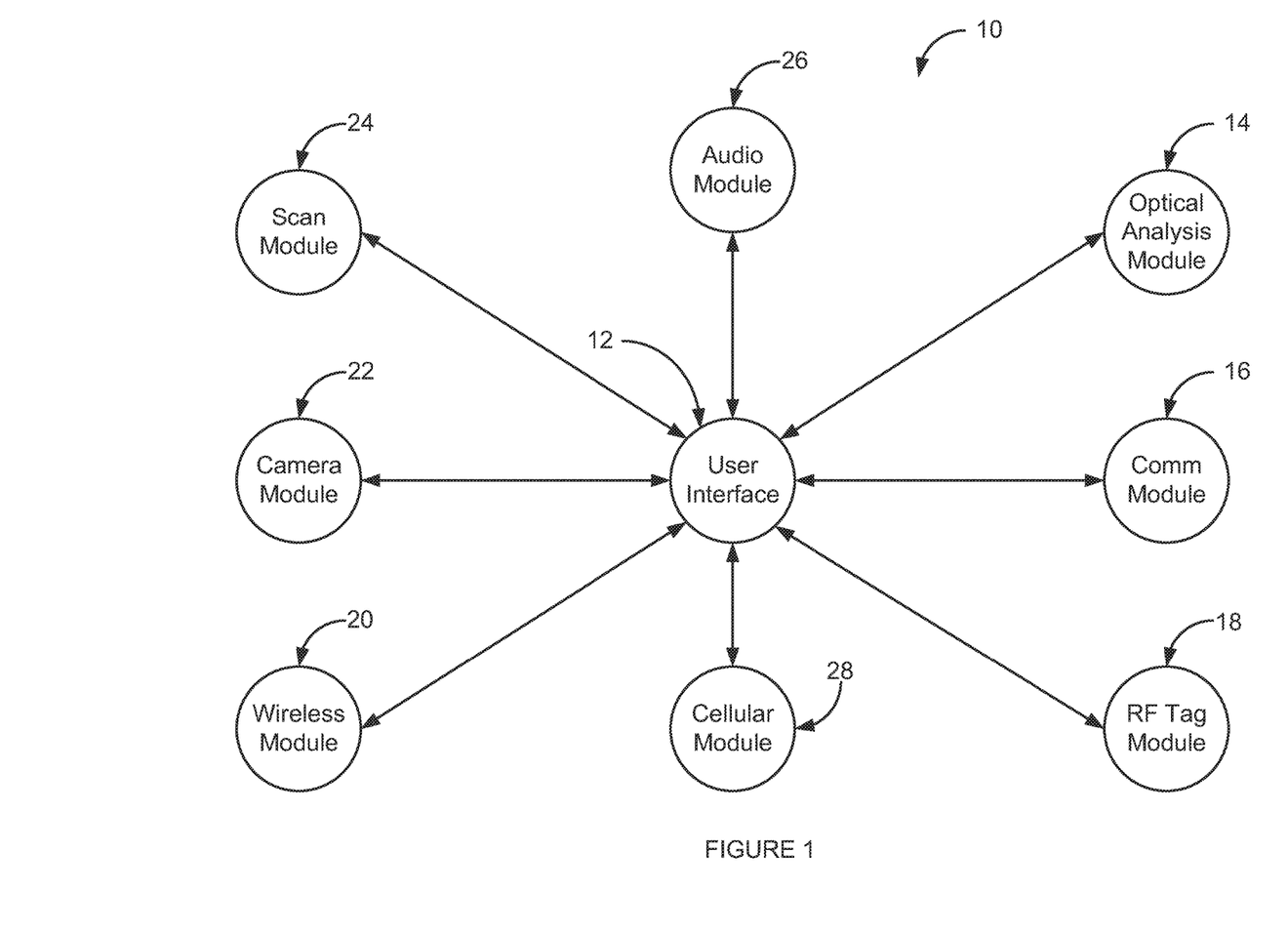
FIG. 1 is a depiction of the functional components of the invention.

Now referencing FIG. 1 where 10 depicts the software components of the invention. In this depiction 12 user interface controls how the process moves from one module to another. Dialog and displays will be presented to the user as informational displays and requests for direction from the various software modules. Captured responses from the user will be sent to requesting software modules.

In this depiction scan module 24 will scan test stick 32/34/35 on both sides as a test stick is inserted into slot 130. Images of the front and back of test stick 32/34/36 are captured by optical edge scanner 128 and saved in memory. Scan module 24 will also scan and capture images of both sides of ID cards as the test administrator inserts an ID card into slot 130. All scanned images associated with a test subject will be saved in memory and written to an event file.

Camera module 22 will capture and save in memory photographs taken by the test administrator of a test subject's face, identifying abnormalities, scars, and tattoos, documents, and other photographs. All photographs associated with a test subject will be saved in memory and written to an event file.

Optical analysis module 14 contains algorithms that analyze photographs of documents and capture text from documents, ID cards, and may perform some form of facial recognition with other photographs stored in memory. Optical analysis module 14 will also, from images of test stick 32/34/36 determine the results of the at the least one test pad 38 and will determine the value of any scan codes such as 40 or 42 or any other type of optical scan code. The results of analysis of photographs, documents, test sticks, or other images associated with a test subject will be saved in memory and written to an event file.

Audio module 26 allows the test administrator to record audio spoken by the test administrator or the test subject or other persons associated with the test subject. Audio that is recorded will be saved in memory and written to an event file.

RF tag module 18 is used to interrogate electronic tags such as RFID tags and Near Field Communications (NFC) tags. RF tag module will send an interrogation signal via antenna 136 residing on the back of device 122 to either RFID tags or NFC tags and receive a coded value form the tag. Values read from tags will be saved in memory and written to an event file Comm module 16 will manage the transfer of event files and other data from device 122 of the invention to networked hosted databases. Comm module 16 will utilize wireless module 20 for actual transport of data to and from the networked hosted databases.

Cellular module 28 allows the test administrator to call and receive calls from personnel remote from where the testing has taken place.

Invention Device Apparatus

Figure 6:
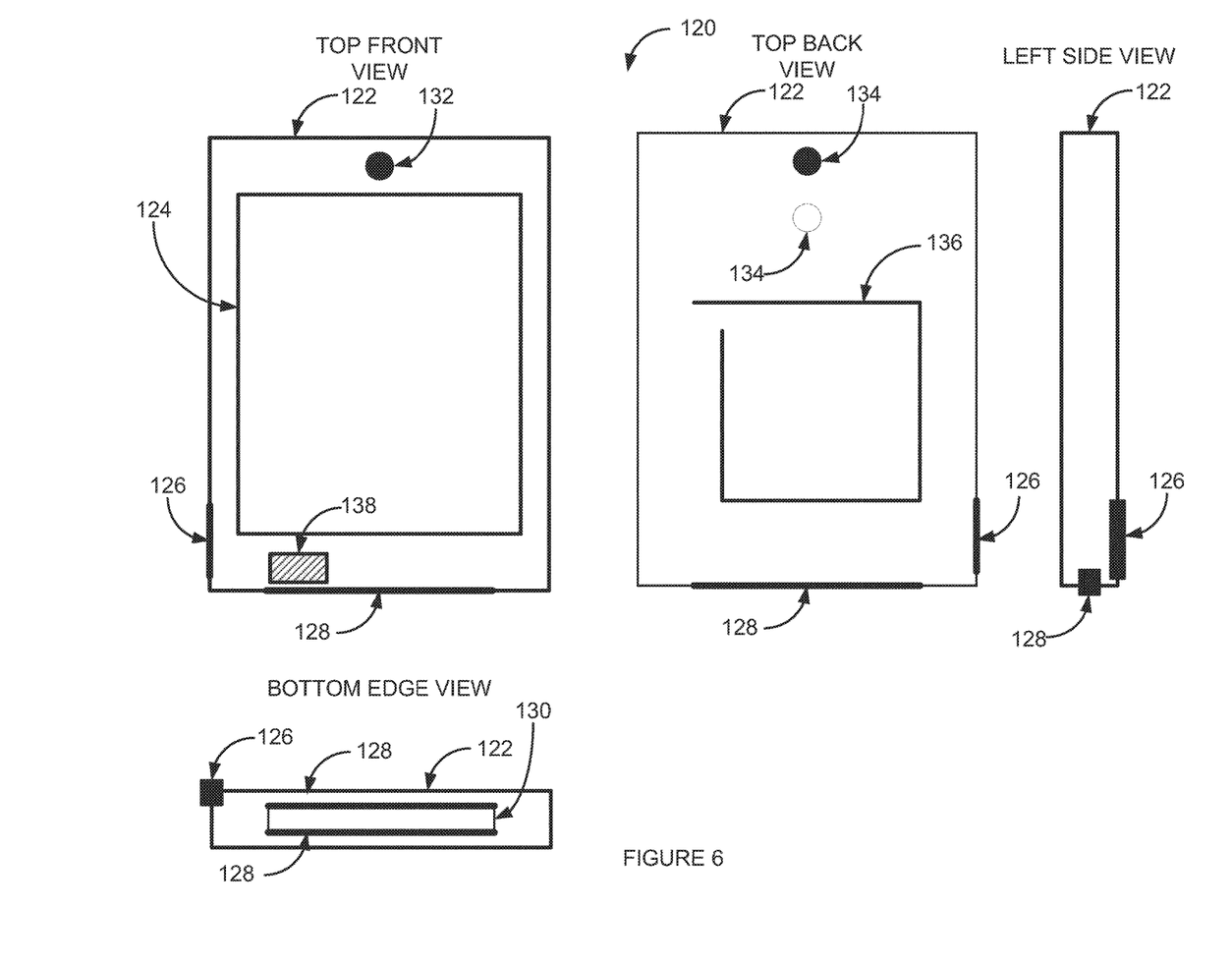
FIG. 6 is a depiction of a top view of the hand held device of the invention.

Now referencing FIG. 6 where 120 is a three view depiction of a handheld device of the invention. In this depiction, 122 is the physical device case. 124 is a touch sensitive display screen used for the user interface. Touch sensitive display screens are well known in the art.

128 is an optical edge scanning device that captures images of test stick 32/34/36 and ID Cards as they are inserted into slot 130 located on the bottom surface of device 122. Note in bottom edge view of device 122, optical edge scanner 128 is composed of two scanner sensors on both the top and bottom of slot 130. Fingerprint scanner 126 is shown residing on the left edge if top front view and on the left side view and bottom edge view. Fingerprint scanners are well known in the art as are optical edge scanners depicted by 128.

Front facing camera 132 and rear facing camera 134 allow the test administrator to take full facial pictures of a test subject and for photographing documents such as ID cards and test sticks (32/34/36) if optical edge scanner is not available or operational. LED flash 136 is use when low light conditions for photography requires supplemental lighting.

Antenna 136 residing on the back surface of device 122 is used to interrogate RFID and NFC tags. When such a tag is available and device 122 is in close proximity too the tag, it will be interrogated and the value returned to RF tag module 18.

Magnetic stripe reader 138 resides shown for clarity resides inside device 122 adjacent to optical edge scanner such that an ID card with a magnetic stripe containing data will be read as the Id card is inserted into slot 130.

Test Sticks

Figure 2:
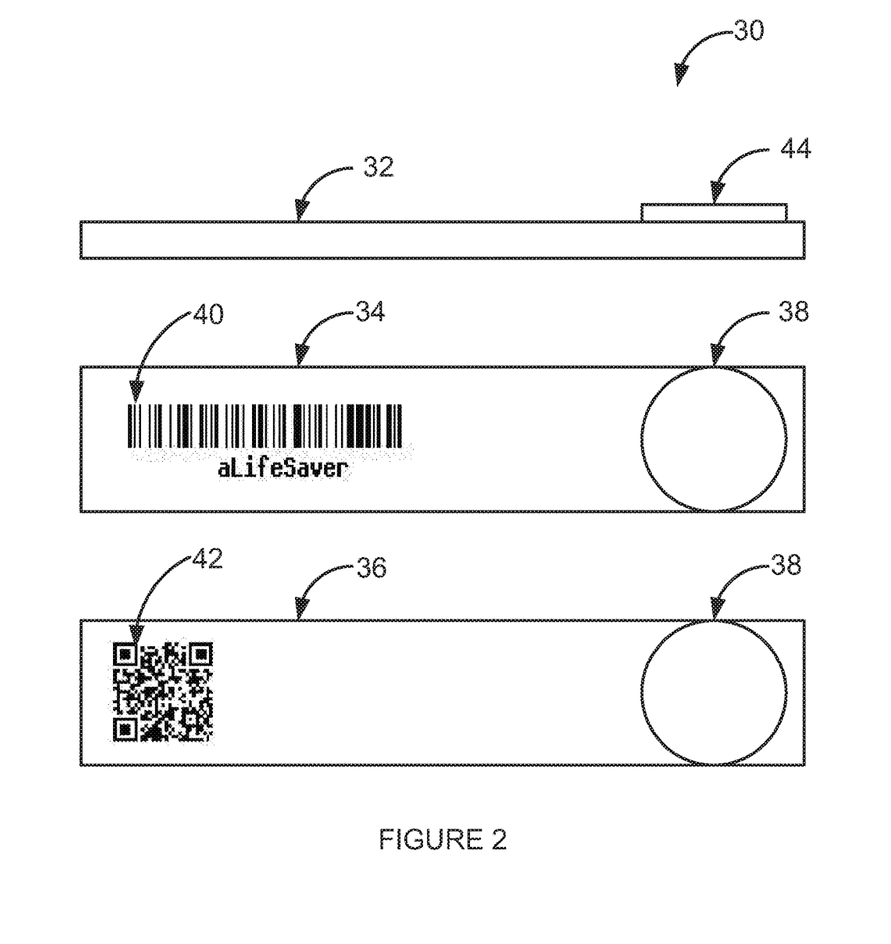
FIG. 2 is a depiction of multiple forms of test sticks.

Now referencing FIG. 2 where 30 depicts three test sticks 32, 34, and 36. Test sticks will have at least one saliva based test pad 34 mounted on the top surface of the stick. The test pad contains a pattern of antigens and/or reagents that change color when in the presence of a specific substance or biological substance. A test stick may have a plurality of test pads mounted to the top surface of the test stick or mounted on both surfaces of a test stick.

All test sticks will also have a unique optically scanable two dimensional scan code. Two of such unique scan codes are 40 and 42. Scan code 40 is a typical two dimensional bar code and 42 is a typical QR two dimensional scan code. Other forms of scan codes are also well known in the art and consist of various geometrical objects such as circles, triangles, and other shapes. Additionally, other two dimensional scan code contain small objects that are different colors. All of these are well known in the art.

Embodiment 1

Figure 3:
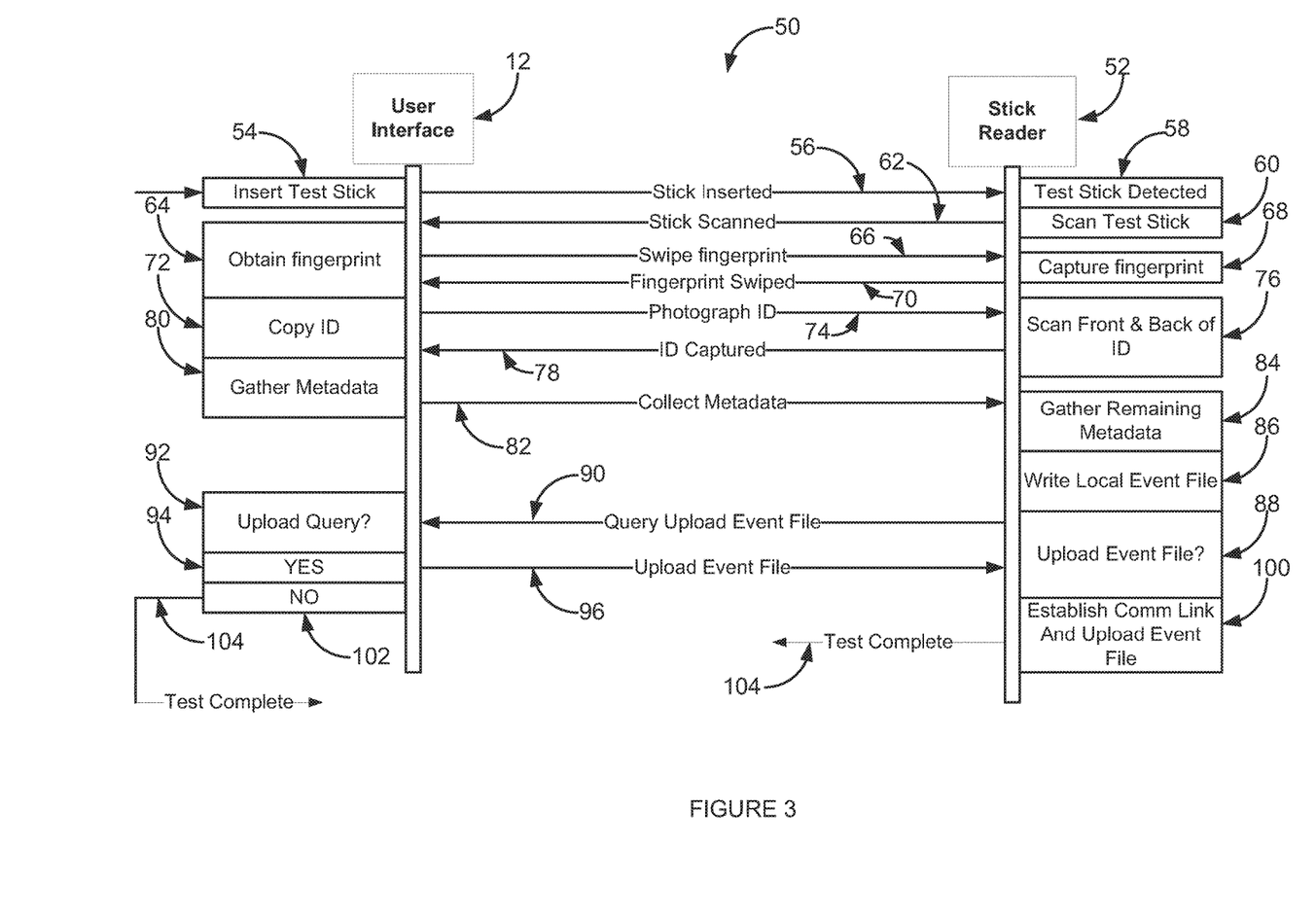
FIG. 3 is a logic flow depiction of embodiment 1

Now referencing FIG. 3 where a logic flow diagram depicts embodiment one of the invention. In this embodiment, user interface 12 depicts the actions of the test administrator and stick reader 52 depicts the actions of the invention occurring under software control.

The logic flow diagram begins with the test administrator at logic block 54 physically inserting a test stick 32/34/36 with at least one saliva based test pad 44 having been saturated with the test subject's saliva. Test stick 32/34/36 will have a two dimensional scan code depicted as 40 or 42

Test stick 32/34/36 will be inserted into slot 130 on the invention. Once the test administrator has inserted test stick 32/34/36 into slot 130, stick inserted signal 56 will be detected by the invention at logic block 58 test stick detected. At this point control will fall through to logic block 60 scan test stick. In this embodiment, optical edge scanner will scan the top and bottom of test stick 32/34/36 as it is being inserted into slot 130. Once an image of test stick 32/34/36 has been captured, logic block 60 scan test stick will send signal 62 stick scanned to logic block 64 obtain finger print.

Logic block 64 will notify the test administrator by displaying dialog on touch sensitive display screen 124 to have the test subject swipe either a single thumbprint or all ten fingers, one at a time, across a swiping fingerprint scanner 128. The user will begin the fingerprint scan by logic block 68 sending signal 66 swipe fingerprint to logic block 68 capture fingerprint. Once the test subject's fingerprint(s) has been captured logic block 68 will send signal 70 fingerprint swiped to logic block 64 obtain fingerprint.

At this point, control will fall through to logic block 72 copy ID. The test administrator will insert the test subject's photo ID, typically a government issued driver's license or ID card. Once the test administrator has inserted the ID card into slot 130 on device 122, optical edge scanner 128 will scan both the front and back of the ID card. The user will then send signal 74 photograph ID to logic block 76 scan front & back of ID. Optical analysis module 14 will then execute a software algorithm and capture the test subject's name, address, ID card number, and any two dimensional scan codes appearing on the front and/or back of the ID card. Additionally, if the card holds a magnetic strip on the front or back, the strip will have been read by a magnetic strip reader 138 when the ID card was inserted into the slot on the invention. Additionally, if the card contains a RFID chip and/or a NFC (near field communications) tag, that RFID chip and/or NFC tag will be read by a RFID reader and/or NFC reader contained within the invention. The data derived from the ID card will be written to the event file. Once the data has been written to the event file logic block 76 will send signal 78 ID captured to logic block 72 copy ID.

At this point, control will fall through to logic block 80 gather metadata. This logic block sends signal 82 collect metadata to logic block 84 gather remaining metadata. This logic block will write a set of additional metadata to the event file. This block of metadata may contain among other data, the test administrator's ID, the GPS location where the test was administered along with the date, time, weather conditions, other personnel attending the administration of the test and other relevant data. Once logic block 84 has gathered the metadata control will fall through to logic block 86 write local event file. After the metadata has been written to the local event file, control will fall through to logic block 88 upload event file?. This logic block will send signal 90 query upload event file to decision logic block 92 upload query?.

Decision logic block 92 upload query? will ask the test administrator if he wants the data for the current test subject uploaded to a network based database. If the test administrator responds that he wants to the data uploaded, control will fall through to response logic block 94 YES. Response logic block 94 YES will send signal 96 upload event file to logic block 100 establish comm link and upload event file. This logic block establishes, through comm. Module 16, any of a number of communications links through cellular link, RF link, Wifi link using wireless module 20 or through a wired network connection. Once the connection is established, logic block 100 will upload the contents of the event file to a network database then exit to test complete 104.

If the test administrator responds that he does not want the data to be uploaded, control will fall through to response logic block 102 NO which then will exit to test complete 104.

Embodiment 2

Figure 4:
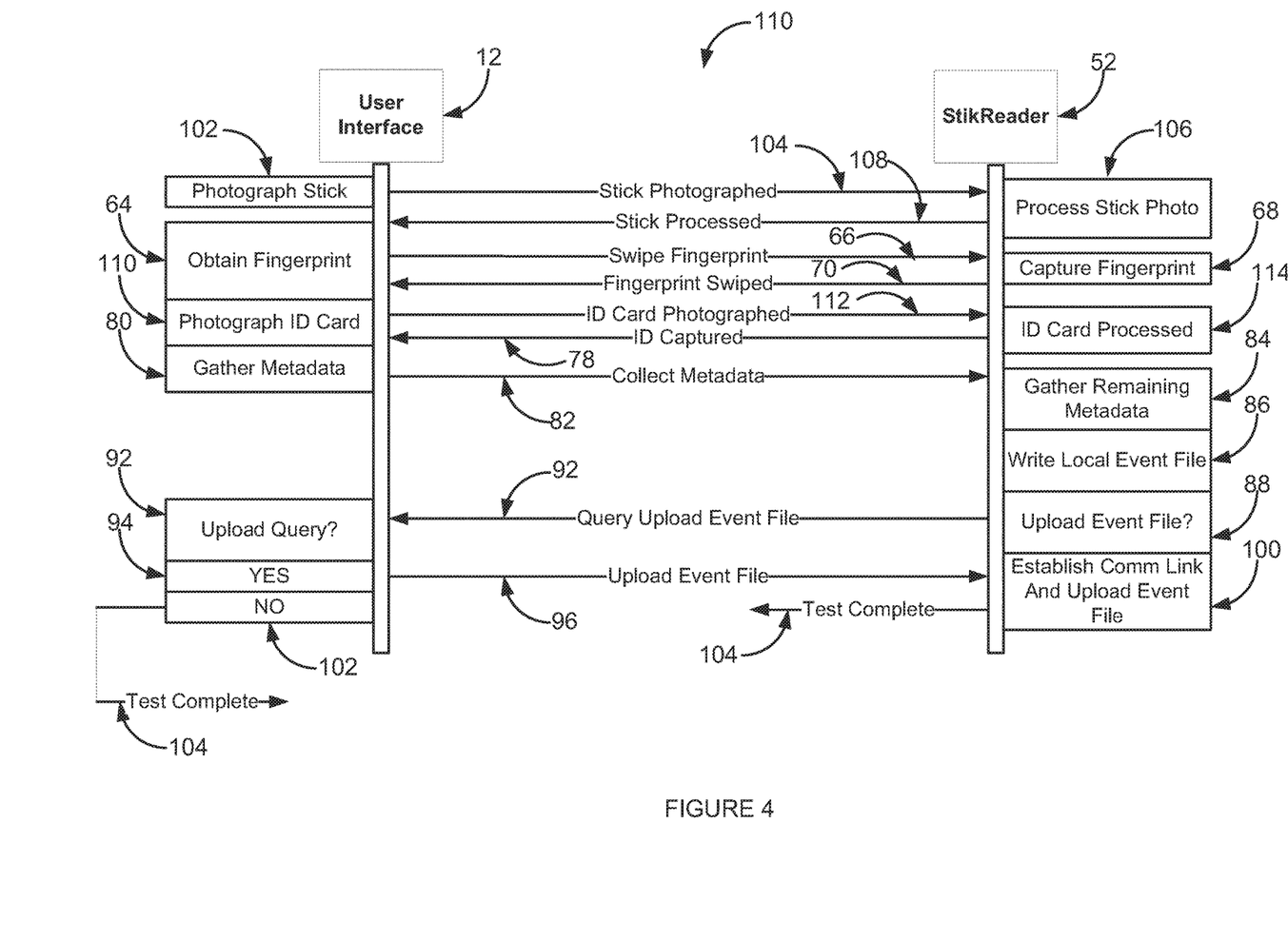
FIG. 4 is a logic flow depiction of embodiment 2

Now referencing FIG. 4 where a logic flow diagram depicts embodiment two of the invention. In this embodiment, user interface 12 depicts the actions of the test administrator and stick reader 52 depicts the actions of the invention occurring under software control.

The logic flow diagram begins with the test administrator at logic block 102 using the rear facing camera 134 on device 122, photograph both sides of test stick 32/34/36 with at least one saliva based test pad 44 having been saturated with the test subject's saliva. Test stick 32/34/36 will have a two dimensional scan code depicted as 40 or 42.

Once the test administrator has taken a photograph of both sides of test stick 32/34/36 signal 104 stick photographed will be sent to logic block 106 process stick photo. Logic block 106 process stick photo will, using optical analysis module 14 analyze the photographic images of test stick 32/34/36 determine the results of the at the least one test pad 38 and will determine the value of any scan codes such as 40 or 42 or any other type of optical scan code. The results of analysis of photographs, documents, test sticks, or other images associated with a test subject will be saved in memory and written to an event file. Logic block 106 will then send signal 108 stick processed to logic block 84 obtain fingerprint.

Logic block 64 obtain fingerprint will notify the test administrator by displaying dialog on touch sensitive display screen 124 to have the test subject swipe either a single thumbprint or all ten fingers, one at a time, across a swiping fingerprint scanner 128. The user will begin the fingerprint scan by logic block 68 sending signal 66 swipe fingerprint to logic block 68 capture fingerprint. Once the test subject's fingerprint(s) has been captured, logic block 68 will send signal 70 fingerprint swiped to logic block 64 obtain fingerprint.

At this point, control will fall through to logic block 110 photograph ID card. The test administrator will photograph both sides of the test subject's photo ID, typically a government issued driver's license or ID card. Once the test administrator has photographed both sides of the test subject's the ID card, signal 112 ID card photographed will be sent to logic block 114 ID card processed. Logic block 114 ID card processed will then, using optical analysis module 14, execute a software algorithm and capture the test subject's name, address, ID card number, and any two dimensional scan codes appearing on the front and/or back of the ID card. Additionally, if the card contains a RFID chip and/or a NFC (near field communications) tag, that RFID chip and/or NFC tag may be read by the test administrator placing device 122 near the ID card. The data derived from the ID card by optical module 40 and any RFID/NFC tags will be written to the event file. Once the data has been written to the event file logic block 114 will send signal 78 ID captured to logic block 110 photograph ID card.

At this point, control will fall through to logic block 80 gather metadata. This logic block sends signal 82 collect metadata to logic block 84 gather remaining metadata. This logic block will gather a set of additional metadata to the event file. This gathered block of metadata may contain among other data, the test administrator's ID, the GPS location where the test was administered along with the date, time, weather conditions, other personnel attending the administration of the test and other relevant data. Once logic block 84 has gathered the metadata control will fall through to logic block 86 write local event file. After the metadata has been written to the local event file, control will fall through to logic block 88 upload event file?. This logic block will send signal 90 query upload event file to decision logic block 92 upload query?.

Decision logic block 92 upload query? will ask the test administrator if he wants the data for the current test subject uploaded to a network based database. If the test administrator responds that he wants to the data uploaded, control will fall through to response logic block 94 YES. Response logic block 94 YES will send signal 96 upload event file to logic block 100 establish comm link and upload event file. This logic block establishes, through comm module 16, any of a number of communications links through cellular link, RF link, Wifi link using wireless module 20 or through a wired network connection. Once the connection is established, logic block 100 will upload the contents of the event file to a network database then exit to test complete 104.

If the test administrator responds that he does not want the data to be uploaded, control will fall through to response logic block 102 NO which then will exit to test complete 104.

Embodiment Three

Figure 5:
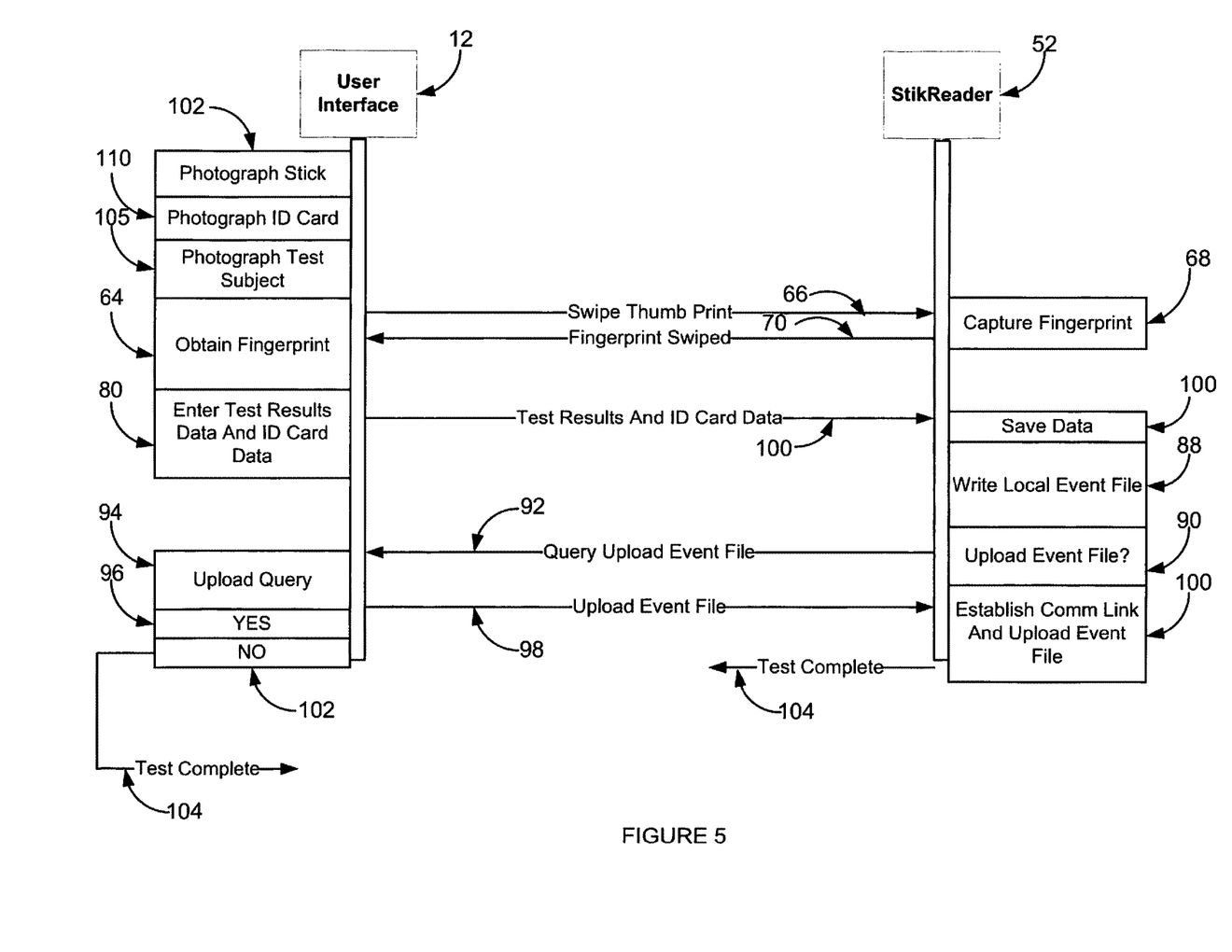
FIG. 5 is a logic flow depiction of embodiment 3

Now referencing FIG. 5 where a logic flow diagram depicts embodiment three of the invention. In this embodiment, user interface 12 depicts the actions of the test administrator and stick reader 52 depicts the actions of the invention occurring under software control.

The logic flow diagram begins with the test administrator at logic block 102 using the rear facing camera 134 on device 122, photographing both sides of test stick 32/34/36 with at least one saliva based test pad 44 having been saturated with the test subject's saliva. Test stick 32/34/36 will have a two dimensional scan code depicted as 40 or 42.

Once the test administrator has taken a photograph of both sides of the test stick, control will fall through to logic bock 110 photograph ID cards. The test administrator will phonograph both sides of the test subject's ID card. Control will then fall through to logic block 105 photograph test subject. The test administrator will phonograph at least a full frontal view of the test subject's face and a full view of each side of the test subject's head. Additionally, the test administrator will photograph any physical amoralities, distinguishing features of the test subject such as scars, tattoos, hair style, clothing, and other features. Control will then fall through to logic block 64 obtain fingerprint. If test device 122 does not have a fingerprint scanner then control will fall through to logic block 80 enter test results data and I card data. If test device 122 does have fingerprint scanner 128, logic block 64 will send signal 88 swipe fingerprint to logic block 68 obtain fingerprint. This logic block will send signal 66 swipe fingerprint to logic block 68 capture fingerprint. At this point the test administrator will, using fingerprint scanner 128, swipe the test subject's thump print or all 10 fingers after which logic block 68 will send signal 70 fingerprint swiped to logic block 64 obtain fingerprint. Control will then fall through to logic block 80 enter test results data and ID card data.

Logic block 80 will allow the test administrator to manually enter the results of the at least one test pad and the data captured from the test subject's ID card into a data entry form displayed by logic block 80 on touch sensitive display screen 124. Once the test administrator has completed entering data, signal 100 test results and ID card data will be sent to logic block 100 save data. Logic block 100 will gather additional metadata such as the test administrator's ID, the GPS location where the test was administered along with the date, time, weather conditions, other personnel attending the administration of the test and other relevant data. After the additional metadata has been gathered, control will fall through to logic block 88 write local event file. This logic block writes the data entered by the test administrator, all of the photographs and the additional metadata. Control will then fall through to logic block 90 upload event file?. This logic block will send signal 92 to decision logic block 94 upload event file?.

Decision logic block 92 upload query? will ask the test administrator if he wants the data for the current test subject uploaded to a network based database. If the test administrator responds that he wants to the data uploaded, control will fall through to response logic block 94 YES. Response logic block 94 YES will send signal 96 upload event file to logic block 100 establish comm link and upload event file. This logic block establishes, through comm module 16, any of a number of communications links through cellular link, RF link, Wifi link using wireless module 20 or through a wired network connection. Once the connection is established, logic block 100 will upload the contents of the event file to a network database then exit to test complete 104.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, external bus 18 may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, displayport, or any other form. This may include laptop or desktop computers, and may also include portable computers, including cell phones, tablets such as the IPAD™ and Android platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventor(s) intend that only those claims which use the words "means for" are intended to be interpreted under 35 USC 112, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

The following definitions are contemplated, however, other meanings for these words may be encompassed within this specification.

DEFINITIONS

Antigen: An antigen is any substance which provokes an adaptive immune response. Antigens are often foreign or toxic to the body which, once in the body, attracts and is bound to a respective and specific antibody. An antigen is a molecule that also induces an immune response in the body. Each antibody of the body is specifically designed to deal with certain antigens. Saliva based testing typically contains one or more antigens per test where the antigens are designed to change color if and when they bind with antibodies contained in the saliva. Antigens are structural molecules that bind specifically to an antibody, but the term now also refers to any molecule or molecular fragment that can be recognized by highly variable antigen receptors (B-cell receptor or T-cell receptor) of the adaptive immune system.

Reagent: A reagent is a substance or compound added to a system in order to bring about a chemical reaction such as a color change. Reagents are compounds or mixtures, usually composed of inorganic or small organic molecules, used to effect a transformation on an organic substrate.

Data Store: A data store is a data repository of a set of integrated data objects. As used in the present invention, a data store is a database consisting of a collection of data records used to save information relating to the results of a diagnostic saliva test. The information saved for these tests may vary depending on the type of test and the administrator administrating the test. A data record may include a photograph of the test stick with the at least one test pad showing the results of the just administrated test, a photograph of the test subject's face, any distinguishing features such as scars, deformities, and tattoos. The data record may also contain such data as GPS location, time and date, weather conditions, and other metadata.

Event File: In the context of the present invention, the event file will be a collection of metadata associated with a just completed saliva based test.

Metadata: In the context of the present invention, metadata is defined as data associated with at least one just completed saliva based test. The metadata may contain such data as GPS location, time and date, weather conditions, and other metadata.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

We claim:

1. A method to capture test results of saliva based tests administered by a test administrator,
   said tests having layers of porous material fixed to a non-reactive test strip of material with each layer containing an antigen and/or reagent designed to change color when in contact with a specific substance in a human or animal saliva sample when said test strip is placed into a mouth of said human or said animal,
   said method comprising:
   receiving, into a test strip reader, a test strop that has been placed into a mouth of a human or animal for a period of time;
   said test strip reader containing an optical scanning device capable of creating a photographic image of said test strip;
   reading an identification card of a human test subject with said test strip reader, said optical scanning device capable of creating a photographic image of both sides of said identification card as an identification card image;
   Photographing said human test subject with a camera built into said test strip reader creating a photograph of the human test subject;
   using a fingerprint scanner for scanning a photographic image of any of the fingerprints scanned by said fingerprint scanner, said fingerprint scanner creates an image of each finger and thumb scanned as fingerprint images;
   using A software module to perform an analysis of said test strip image created by said optical scanning device, said analysis forms the results of said test strip, said analysis saved in a local event file;
   using the software module that performs an analysis of said identification card image created by said optical scanning device, said analysis forms textual data relating to said human test subject, said textual data saved in a local event file;

using the software module that performs an analysis of said identification card image created by said optical scanning device, said analysis forms textual data relating to said human test subject, said textual data saved in a local event file;

using the software module that writes said fingerprint images to a local event file;

using the software module that gathers metadata relating to said human test subject and writing said metadata to said local event file;

using the software module that wirelessly transfers said local event file to a network hosted database.

2. A method to capture test results of saliva based tests administered by a test administrator, said tests having layers of porous material fixed to a non-reactive test strip of material with each layer containing an antigen and/or reagent designed to change color when in contact with a specific substance in a human or animal saliva sample when said test strip is placed into a mouth of said human or said animal, said method comprising:

photographing both sides of a test strip that has been placed into a mouth of a human or animal and removed after a predetermined period of time with a camera built into a test strip reader creating an image of both sides of said test strip;

photographing both sides of an identification card of a human test subject with a camera built into said test strip reader creating an image of both sides of said identification card s an identification card image;

Photographing said human test subject with a camera built into said test strip reader creating a photograph of the human test subject;

performing an analysis of said test strip image created by said test administrator photographing said test strip, said analysis forms the results of said test strip, said analysis saved in a local event file;

performing an analysis of said identification card image created by said test administrator photographing said identification card, said analysis forms textual data relating to said human test subject, said textual data saved in a local event file;

gathering metadata relating to said human test subject and storing said metadata into the local event file; and wirelessly transferring said local event file to a network hosted database.

3. The method as in claim 2, wherein said metadata includes a test administrator's ID, GPS location where said test strip was administered along with date, time, weather conditions, other personnel attending the administration of the test.

4. The method as in claim 2, further comprising
obtaining fingerprint images from said human test subject;
and writing said fingerprint images to the local event file.

5. A method to capture test results of saliva based tests administered by a test administrator, said tests having layers of porous material fixed to a non-reactive test strip of material with each layer containing an antigen and/or reagent designed to change color when in contact with a specific substance in a human or animal saliva sample when said test strip is placed into a mouth of said human or said animal, said method comprising:

photographing a test strip which has been placed into a mouth of a human or animal, using a camera built into a test strip reader to create a photographic image of said test strip;

photographing an identification card from said test subject with the camera built into said test strip reader and creating photographic images of both sides of said identification card;

Photographing said human test subject with the camera built into said test strip reader creating a photograph of the human test subject;

using A software module that performs an analysis of said photographic images of both sides of said test strip created by said test administrator photographing said test strip, said analysis forms the results of said test strip, said analysis saved in a local event file;

using the software module that performs an analysis of said photographic images of both sides of said identification card created by said test administrator photographing both sides of said identification card, said analysis creating textual data relating to said human test subject, said textual data saved in a local event file;

using the software module that gathers metadata relating to said human test subject, and storing said metadata in said local event file; and using the software module that wirelessly transfers said local event file to a network hosted database.

6. The method as in claim 5, wherein said photographing comprises photographing both sides of the test strip.

7. The method as in claim 5, wherein said metadata includes a test administrator's ID, GPS location where said test strip was administered along with date, time, weather conditions, other personnel attending the administration of the test and writes said relevant data to said local event file.

8. The method as in claim 1, wherein said metadata includes a test administrator's ID, GPS location where said test strip was administered along with date, time, weather conditions, other personnel attending the administration of the test and other relevant data and writes said relevant data to said local event file.

* * * * *